US009658185B2

(12) United States Patent
Paggel et al.

(10) Patent No.: US 9,658,185 B2
(45) Date of Patent: May 23, 2017

(54) METHOD AND APPARATUS FOR OPERATING A LINEAR LAMBDA PROBE

(71) Applicants: Jens Paggel, Abensberg (DE); Sirko Schlegel, Neutraubling (DE)

(72) Inventors: Jens Paggel, Abensberg (DE); Sirko Schlegel, Neutraubling (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 486 days.

(21) Appl. No.: 14/360,665

(22) PCT Filed: Nov. 21, 2012

(86) PCT No.: PCT/EP2012/073157
§ 371 (c)(1),
(2) Date: May 27, 2014

(87) PCT Pub. No.: WO2013/079368
PCT Pub. Date: Jun. 6, 2013

(65) Prior Publication Data
US 2014/0367276 A1 Dec. 18, 2014

(30) Foreign Application Priority Data
Nov. 29, 2011 (DE) .................. 10 2011 087 310

(51) Int. Cl.
*G01N 27/41* (2006.01)
*G01M 15/10* (2006.01)
(Continued)

(52) U.S. Cl.
CPC ......... *G01N 27/41* (2013.01); *F02D 41/1441* (2013.01); *F02D 41/1456* (2013.01);
(Continued)

(58) Field of Classification Search
CPC . G01N 27/41; G01N 27/4065; G01M 15/108; F02D 41/1411; F02D 41/1454; F02D 41/1456; F01N 2560/025
See application file for complete search history.

(56) References Cited

U.S. PATENT DOCUMENTS 4,658,790 A    4/1987  Kitahara ................. 123/693
7,780,829 B2   8/2010  Diehl et al. ............. 204/429
(Continued)

FOREIGN PATENT DOCUMENTS

DE          3515588 A1   11/1985  ............ F02D 41/14
DE      102004048318 A1    4/2006  ........... G01N 27/407
WO        2013/079368 A1   6/2013  ........... G01N 27/406

OTHER PUBLICATIONS

Basshuysen, Richard van et al., "Handbuch Verbrennungsmotor: Grundlagen, Komponenten, Systeme, Perspektiven," Book, Wiesbaden: Vieweg Verglag, pp. 559-561, 568-570, 589 (13 pages total) (German language w/ English translation), Jan. 1, 2002.
(Continued)

*Primary Examiner* — Gurpreet Kaur
(74) *Attorney, Agent, or Firm* — Slayden Grubert Beard PLLC

(57) ABSTRACT

A signal from a linear lambda probe, which signal is meant to represent an air/fuel ratio for the gas flowing in the exhaust section, specifically prior to combustion of said gas, is determined based on a pump current. A difference signal is formed based on a difference between a pump voltage signal and a Nernst voltage signal. An offset error in the measured signal is determined based on the difference signal for an approximately stoichiometrically prescribed raw setpoint value for the air/fuel ratio, with a setpoint value for the air/fuel ratio being determined based on the raw setpoint value and a forced excitation signal.

12 Claims, 8 Drawing Sheets

(51) Int. Cl.
    *G01N 27/406* (2006.01)
    *F02D 41/14* (2006.01)
    *F02D 41/22* (2006.01)
(52) U.S. Cl.
    CPC ......... *F02D 41/222* (2013.01); *G01M 15/108* (2013.01); *G01N 27/4065* (2013.01); *F01N 2560/025* (2013.01); *Y02T 10/40* (2013.01)

(56) References Cited

U.S. PATENT DOCUMENTS

| | | | |
|---|---|---|---|
| 2005/0173265 A1 | 8/2005 | Stahl | 205/783.5 |
| 2007/0119719 A1* | 5/2007 | Diehl | G01N 27/419 205/785.5 |

OTHER PUBLICATIONS

International Search Report and Written Opinion, Application No. PCT/EP2012/073157, 23 pages, Feb. 25, 2013.

* cited by examiner

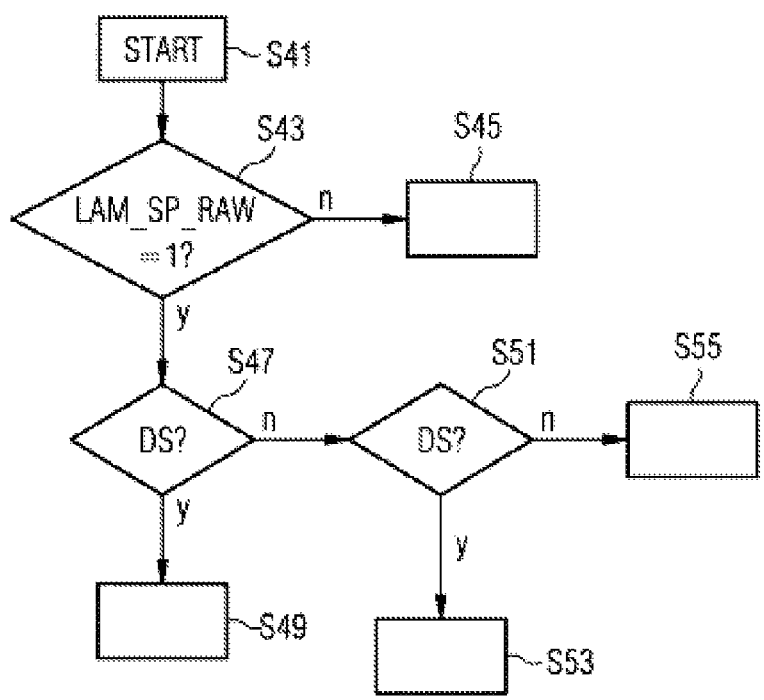

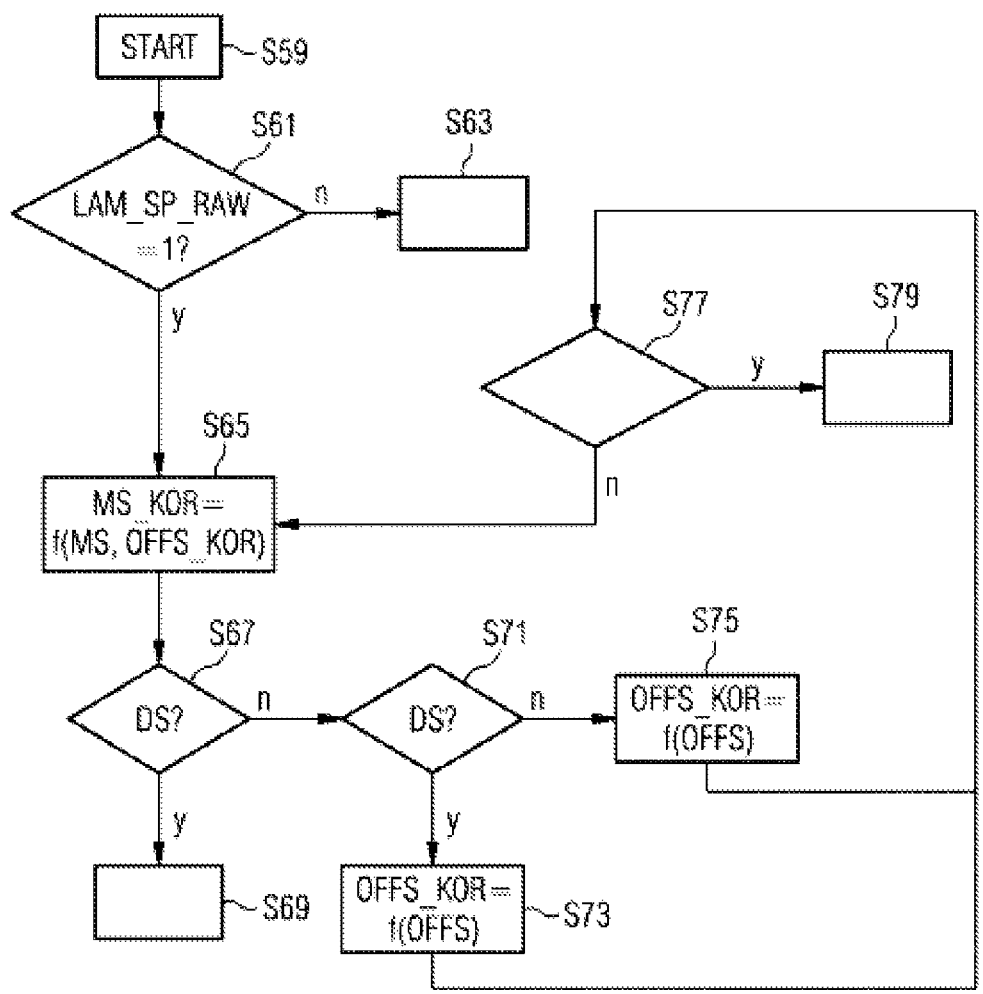

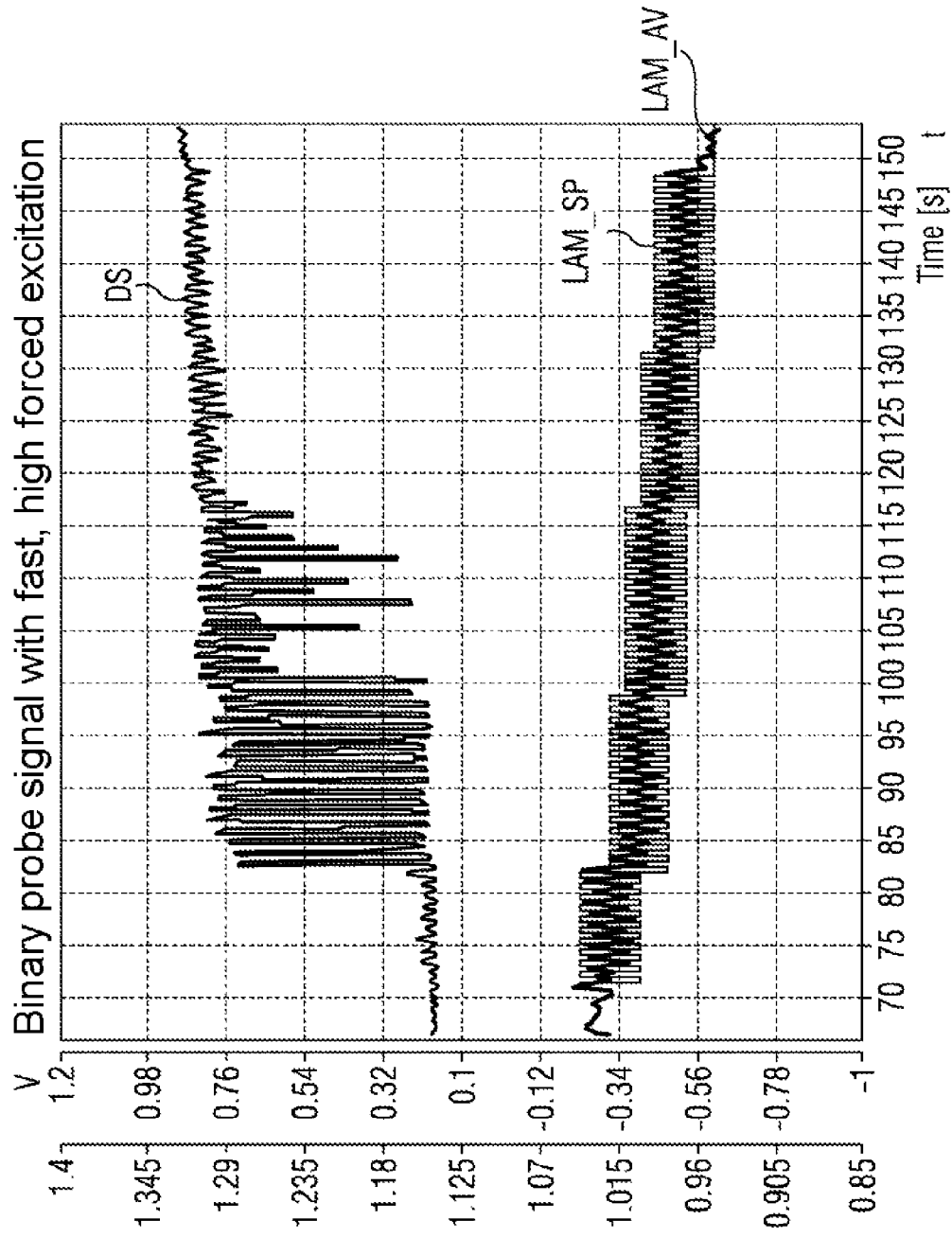

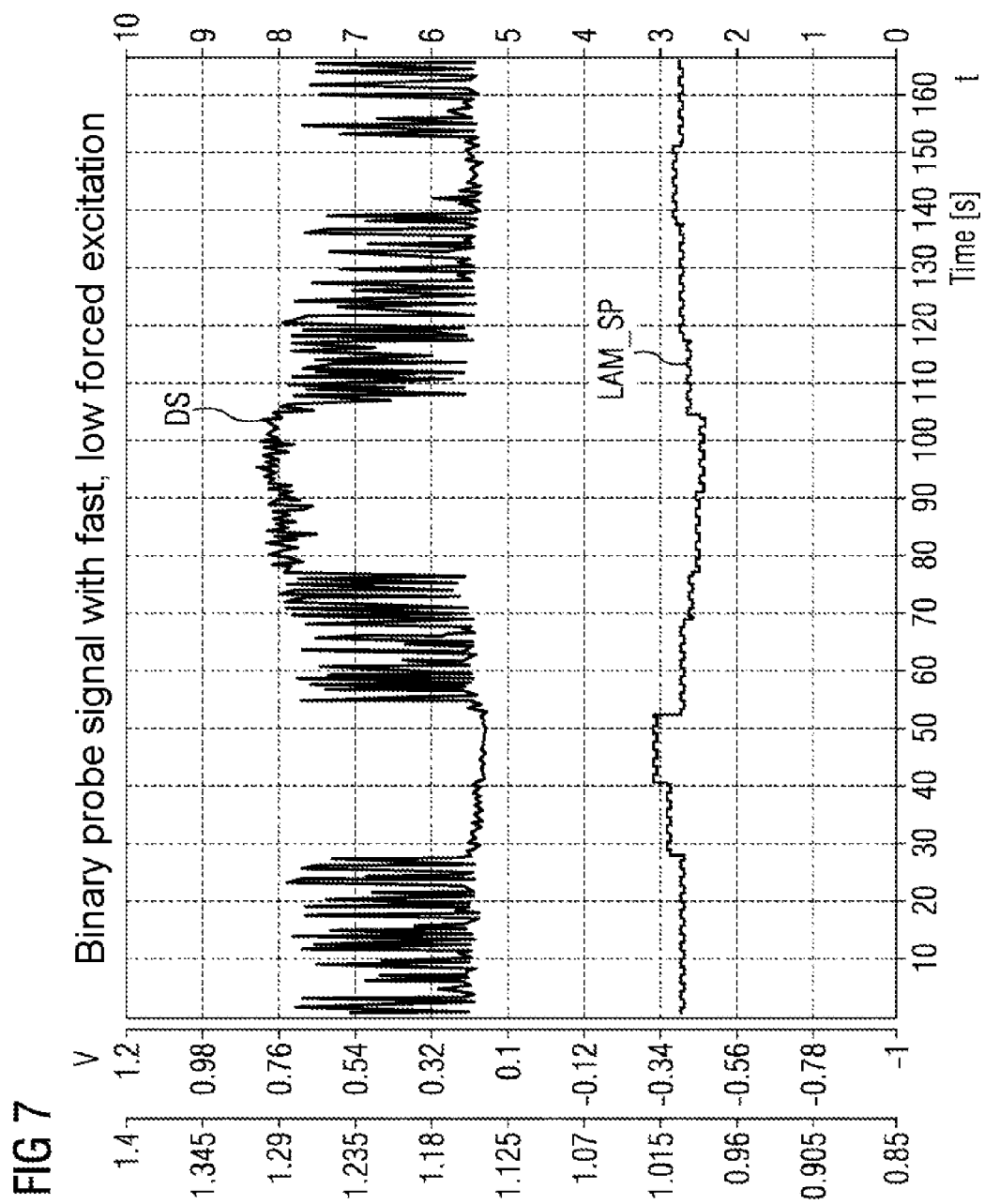

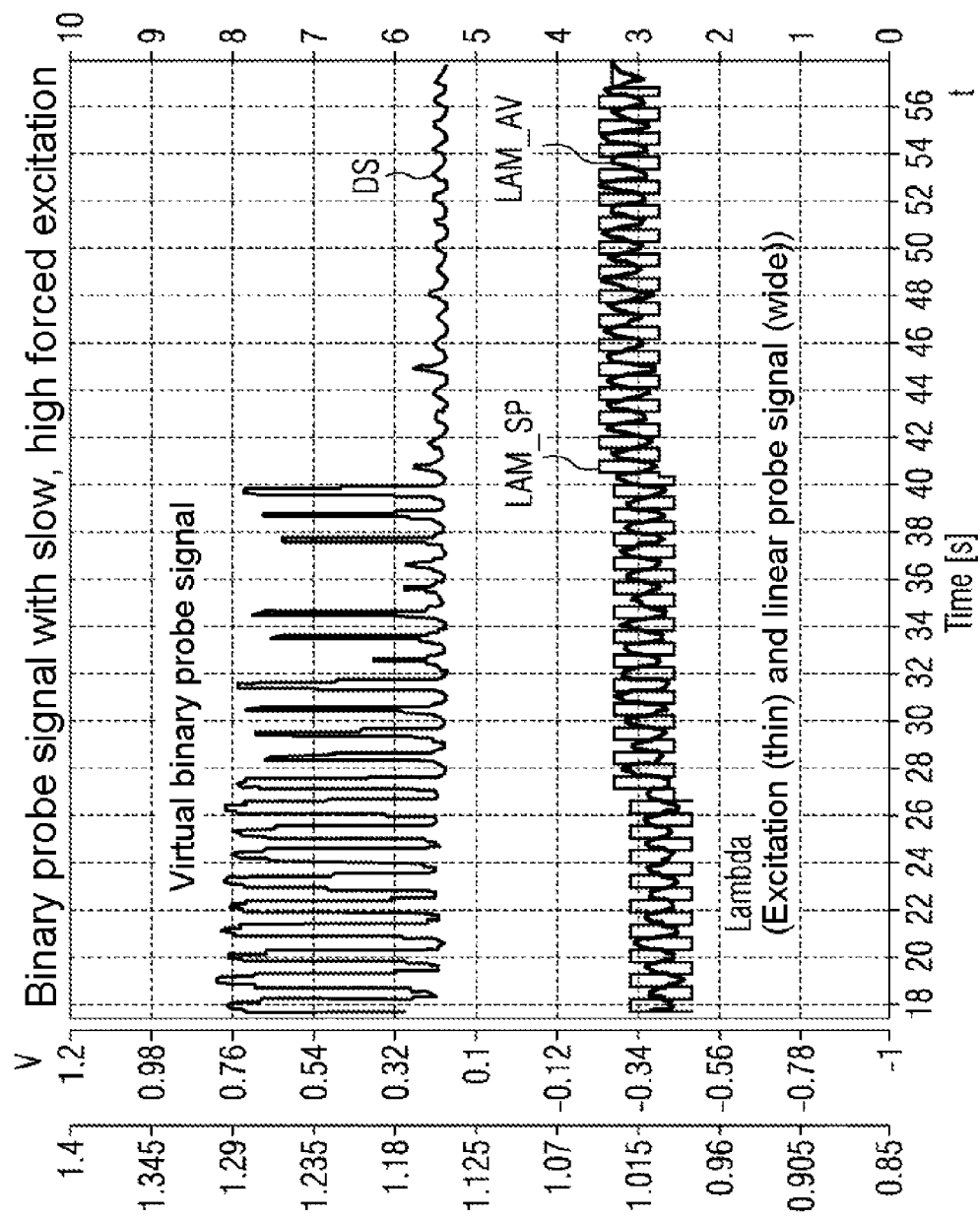

METHOD AND APPARATUS FOR OPERATING A LINEAR LAMBDA PROBE

CROSS-REFERENCE TO RELATED APPLICATIONS

This application is a U.S. National Stage application of International Application No. PCT/EP2012/073157 filed Nov. 21, 2012, which designates the United States of America, and claims priority to DE Application No. 10 2011 087 310.4 filed Nov. 29, 2011, the contents of which are hereby incorporated by reference in their entirety.

TECHNICAL FIELD

The invention relates to a method and an apparatus for operating a linear lambda probe arranged in an exhaust section of an internal combustion engine.

BACKGROUND

Ever stricter legal regulations regarding permissible pollutant emissions from motor vehicles with internal combustion engines arranged therein make it necessary to minimize the pollutant emissions during operation of the internal combustion engine. In one approach, this can be done by reducing the pollutant emissions that arise during the combustion of the air/fuel mixture in the respective cylinder of the internal combustion engine. Another approach involves using, in internal combustion engines, exhaust gas after treatment systems which convert the pollutant emissions generated during the combustion process of the air/fuel mixture in the respective cylinders into non-harmful substances. For this purpose, use is made of exhaust gas catalytic converters which convert carbon monoxide, hydrocarbons and nitrogen oxides into non-harmful substances.

Both the targeted influencing of the generation of pollutant emissions during combustion and also the conversion of the pollutant components with a high efficiency by means of the exhaust gas catalytic converter presuppose a very precisely set air/fuel ratio in the respective cylinder. In this connection, use is made of lambda probes, for example, in particular linear lambda probes, to be precise in the context of lambda control. A linear lambda probe can also be designated as a wide-band probe.

SUMMARY

One embodiment provides a method for operating a linear lambda probe arranged in an exhaust section of an internal combustion engine, comprising a first electrode arranged on the exhaust gas side and a second and third electrode, each of which is arranged adjacent to a measurement chamber, and a fourth electrode, which is arranged adjacent to a reference air volume, wherein solid electrolytes are respectively situated between the first and second electrodes and between the third and fourth electrodes and a diffusion barrier is formed between the free volume of the measurement chamber and the exhaust section, wherein a potential difference between the first and second electrodes forms a pump voltage signal and a potential difference between the fourth and third electrodes forms a Nernst voltage signal, wherein: a measurement signal of the linear lambda probe, which measurement signal is intended to represent an air/fuel ratio of the gas flowing in the exhaust section, to be precise before the combustion of said gas, is determined depending on a pump current impressed between the first and second electrodes, a difference signal is formed depending on a difference between the pump voltage signal and the Nernst voltage signal, and an offset error of the measurement signal is determined depending on the difference signal in the case of an approximately stoichiometrically predefined raw setpoint value of the air/fuel ratio, wherein a setpoint value of the air/fuel ratio is determined depending on the raw setpoint value and a forced excitation signal.

Another embodiment provides a method for operating a linear lambda probe arranged in an exhaust section of an internal combustion engine, comprising a first electrode arranged on the exhaust gas side and a second and third electrode, each of which is arranged adjacent to a measurement chamber, and a fourth electrode, which is arranged adjacent to a reference air volume, wherein solid electrolytes are respectively situated between the first and second electrodes and between the third and fourth electrodes and a diffusion barrier is formed between the free volume of the measurement chamber and the exhaust section, wherein a potential difference between the first and second electrodes forms a pump voltage signal and a potential difference between the fourth and third electrodes forms a Nernst voltage signal, wherein: a measurement signal of the linear lambda probe, which measurement signal is intended to represent an air/fuel ratio of the gas flowing in the exhaust section, to be precise before the combustion of said gas, is determined depending on a pump current impressed between the first and second electrodes, a corrected measurement signal is determined depending on the measurement signal and an offset correction value, a difference signal is formed depending on a difference between the pump voltage signal and the Nernst voltage signal, an offset of the corrected measurement signal is determined depending on the difference signal in the case of an approximately stoichiometrically predefined raw setpoint value of the air/fuel ratio, wherein a setpoint value of the air/fuel ratio is determined depending on the raw setpoint value and a forced excitation signal, and the offset correction value is adapted depending on the offset determined.

In a further embodiment, the offset of the measurement signal is determined depending on a fluctuation characteristic value of the difference signal.

In a further embodiment, in the case of a short period duration of the forced excitation signal, a check is made to ascertain whether the fluctuation characteristic value exceeds a first threshold value, and, if the fluctuation characteristic value does not exceed the first threshold value, the offset error or offset is determined depending on the difference signal.

In a further embodiment, in the case of a long period duration of the forced excitation signal, a check is made to ascertain whether the difference signal correlates with the setpoint value of the air/fuel ratio, and, if no predefined correlation is identified, the offset error or the offset is determined depending on the difference signal.

Another embodiment provides an apparatus for operating a linear lambda probe, which is designed to carry a method as disclosed above.

Another embodiment provides an apparatus for operating a linear lambda probe, arranged in an exhaust section of an internal combustion engine, wherein the apparatus is designed to carry out a method as disclosed above.

BRIEF DESCRIPTION OF THE DRAWINGS

Example embodiments of the invention are explained in greater detail below with reference to the schematic drawings, in which:

FIG. 4 shows a flow chart of a third program for operating the linear lambda probe, FIG. 5 shows a flow chart of a fourth program for operating the linear lambda probe, FIG. 6 shows a first signal profile, FIG. 7 shows a second signal profile, and FIG. 8 shows a third signal profile.

DETAILED DESCRIPTION

Figure 1:
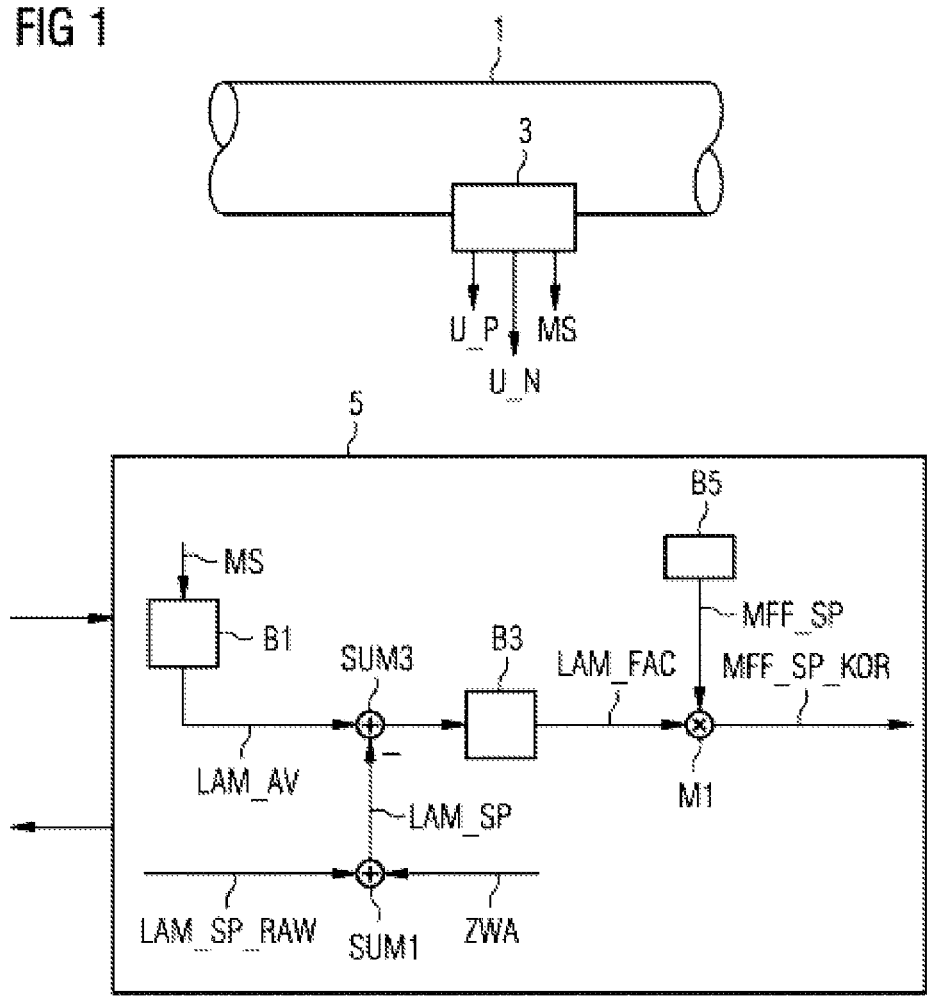
FIG. 1 shows an exhaust section of an internal combustion engine with an assigned control apparatus.
Figure 2:
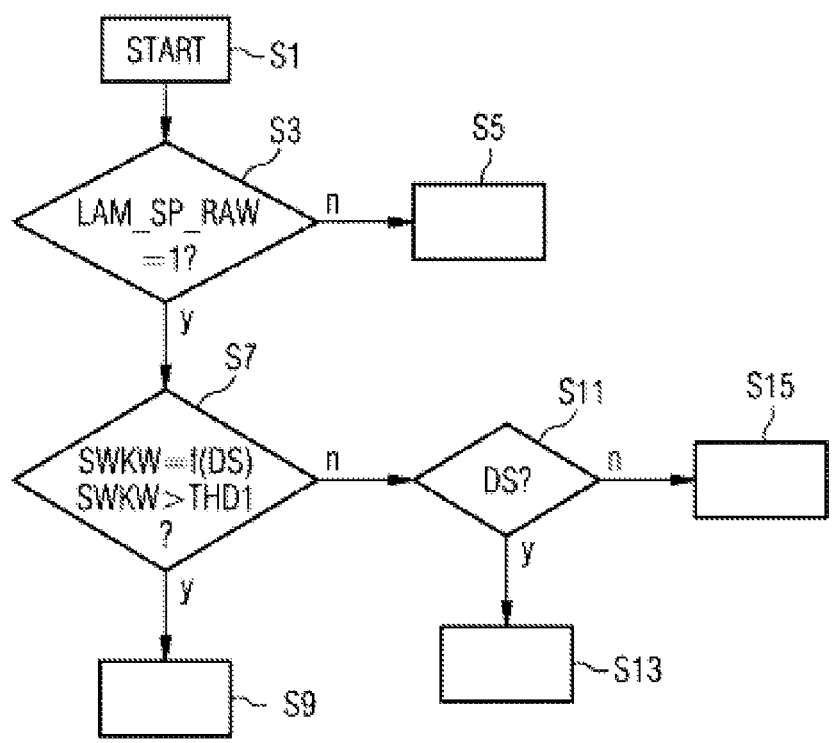
FIG. 2 shows a flow chart of a first program for operating the linear lambda probe.

Embodiments of the invention provide a method and an apparatus for providing reliable and low-emission operation of an internal combustion engine.

Some embodiments provide a method and a corresponding apparatus for operating a linear lambda probe arranged in an exhaust section of an internal combustion engine, comprising a first electrode arranged on the exhaust gas side and a second and third electrode, each of which is arranged adjacent to a measurement chamber, and a fourth electrode, which is arranged adjacent to a reference volume, wherein solid electrolytes are respectively situated between the first and second electrodes and between the third and fourth electrodes and a diffusion barrier is formed between the free volume of the measurement chamber and the exhaust section, wherein a potential difference between the first and second electrodes forms a pump voltage signal and a potential difference between the fourth and third electrodes forms a Nernst voltage signal.

A measurement signal of the linear lambda probe, which measurement signal is intended to represent an air/fuel ratio of the gas flowing in the exhaust section, to be precise before the combustion of said gas, is determined depending on a pump current impressed between the first and second electrodes. A difference signal is formed depending on a difference between the pump voltage signal and the Nernst voltage signal. An offset error of the measurement signal is determined depending on the difference signal in the case of an approximately stoichiometrically predefined raw setpoint value of the air/fuel ratio.

A setpoint value of the air/fuel ratio is determined depending on the raw setpoint value and a forced excitation signal. The forced excitation signal has, in particular, a rectangular periodic signal profile. The predefined raw setpoint value is approximately stoichiometric if it lies in a narrow range around the stoichiometric air/fuel ratio, that is to say deviates therefrom for example by only a few percent, thus for example approximately +/−5% or in particular approximately +/−3%.

In this connection, use is made of the insight that the difference signal has, in principle, signal properties similar to those of the measurement signal of a binary lambda probe. In this regard, small fluctuations of the setpoint value of the air/fuel ratio around the stoichiometric ratio, with the aid of the difference signal, enable a simple detection of the actual stoichiometric air/fuel ratio and thus a determination of the offset of the measurement signal of the linear lambda probe.

The offset error thus determined can be used for example in the context of a diagnosis of the linear lambda probe. In this connection, by way of example, a diagnosis with regard to the offset of the measurement signal can be carried out in addition or as an alternative to a corresponding diagnosis by means of a further lambda probe, which is for example a binary lambda probe and is arranged for example downstream of an exhaust gas catalytic converter in the exhaust section. In this regard, in principle, by way of example, such a second lambda probe can then also be dispensed with.

Some embodiments provide a method and a corresponding apparatus for operating a linear lambda probe arranged in an exhaust section of an internal combustion engine, comprising a first electrode arranged on the exhaust gas side and a second and third electrode, each of which is arranged adjacent to a measurement chamber, and a fourth electrode, which is arranged adjacent to a reference volume, wherein solid electrolytes are respectively situated between the first and second electrodes and between the third and fourth electrodes and a diffusion barrier is formed between the free volume of the measurement chamber and the exhaust section, wherein a potential difference between the first and second electrodes forms a pump voltage signal and a potential difference between the fourth and third electrodes forms a Nernst voltage signal.

A measurement signal of the linear lambda probe, which measurement signal is intended to represent an air/fuel ratio of the gas flowing in the exhaust section, to be precise before the combustion of said gas, is determined depending on a pump current impressed between the first and second electrodes.

A corrected measurement signal is determined depending on the measurement signal and an offset correction value. The corrected measurement signal is then used for example in the context of lambda control.

A difference signal is formed depending on a difference between the pump voltage signal and the Nernst voltage signal. An offset of the corrected measurement signal is determined depending on the difference signal in the case of an approximately stoichiometrically predefined raw setpoint value of the air/fuel ratio. A setpoint value of the air/fuel ratio is determined depending on the raw setpoint value and a forced excitation signal. The offset correction value is adapted depending on the offset determined. The explanations with regard to the first aspect analogously apply to the second aspect as well.

As a result of the correction of the measurement signal by means of the offset correction value, an offset compensation can thus be carried out in a simple manner and, in connection with the use of the corrected measurement signal in lambda control, for example, a high quality of the control can thus be achieved, even in the case of values of the absolute offset of the linear lambda probe that vary during the operation of said linear lambda probe.

In principle, with regard to the second aspect, the offset and/or the offset correction value can also be used for example in the context of a diagnosis of the linear lambda probe.

In accordance with one configuration, the offset error of the measurement signal or the offset of the corrected measurement signal is determined depending on a fluctuation characteristic value of the difference signal. The fluctuation characteristic value is in particular representative of an amplitude of fluctuations of the difference signal and, if appropriate, also with regard to a temporal frequency of the fluctuations of the difference signal, if appropriate with an at least predefined amplitude. In this way, in particular a range of the actual air/fuel ratio which is approximately stoichiometric can be identified or distinguished from an air/fuel ratio deviating therefrom.

In accordance with a further configuration, in the case of a short period duration of the forced excitation signal, a check is made to ascertain whether the fluctuation characteristic value exceeds a first threshold value, and, if the fluctuation characteristic value does not exceed the first threshold value, the offset error or offset is determined depending on the difference signal. In the case of the short period duration of the forced excitation signal, with regard to the sensor-inherent behavior of the linear lambda probe, the difference signal can follow the profile of the setpoint value of the air/fuel ratio only incompletely. However, the fluctuation characteristic value exceeds a suitably predefined first threshold value if the actual air/fuel ratio corresponds approximately to the stoichiometric ratio, in particular exactly to the stoichiometric ratio. This can then be utilized in order, in the case where the first threshold value is not exceeded, then to determine the offset error or offset depending on the difference signal.

In accordance with a further configuration, in the case of a long period duration of the forced excitation signal, a check is made to ascertain whether the difference signal correlates with the setpoint value of the air/fuel ratio, and, if no predefined correlation is identified, the offset error or offset is determined depending on the difference signal. In this connection, use is made of the insight that, in the case of a correspondingly long period duration in comparison with the short period duration, on account of the sensor-internal properties, the difference signal is suitably correlated with the setpoint value of the air/fuel ratio and thus also with the forced excitation thereof, to be precise in a narrow range in which the actual air/fuel ratio fluctuates around the stoichiometric ratio in accordance with the forced excitation.

An internal combustion engine has a plurality of cylinders, each of which is assigned at least one gas inlet valve by means of which a supply of air is adjustable. Furthermore, the respective cylinder is assigned a respective injection valve by means of which fuel can be supplied to a combustion chamber of the respective cylinder. Furthermore, the internal combustion engine has an exhaust section 1 (FIG. 1), via which exhaust gases can be discharged from the respective combustion chambers of the cylinders. In this connection, the internal combustion engine has respective gas outlet valves by means of which the discharge of the exhaust gas from the combustion chambers into the exhaust section 1 is controllable.

A linear lambda probe 3 is arranged in the exhaust section 1. A basic construction of such a linear exhaust gas probe is described for example in the Handbuch Verbrennungsmotor [Handbook of Internal Combustion Engines], $2^{nd}$ Edition, Jun. 2002, Friedrich Vieweg & Sohn Verlagsgesellschaft mbH, Braunschweig/Wiesbaden, ISBN 3-528-13933-1 on page 589, the content of which in this regard is hereby incorporated.

The linear lambda probe 3 has a first electrode arranged on the exhaust gas side. It furthermore has a second and third electrode, each of which is arranged adjacent to a measurement chamber. It furthermore has a fourth electrode, which is arranged adjacent to a reference air volume. Solid electrolytes, in particular composed of oxygen-ion-conducting zirconium dioxide, are respectively situated between the first and second electrodes and between the third and fourth electrodes. Furthermore, a diffusion barrier is formed between the free volume of the measurement chamber and the exhaust section. A potential difference between the first and second electrodes forms a pump voltage signal $U\_P$. A potential difference between the fourth and third electrodes forms a Nernst voltage signal $U\_N$. A measurement signal MS of the linear lambda probe 3, which measurement signal is intended to represent an air/fuel ratio of the gas flowing in the exhaust section, to be precise before the combustion of said gas, is determined depending on a pump current $I\_P$ impressed between the first and second electrodes.

Furthermore, a control apparatus 5 is provided, to which various input signals are fed, in particular from various sensors assigned to the internal combustion engine. In this regard, inter alia, the pump voltage signal $U\_P$, the Nernst voltage signal $U\_N$ and the measurement signal MS of the linear lambda probe 3 are fed to the control apparatus on the input side. The control apparatus 5 is designed to generate, depending on the measurement signal or signals fed to it, actuating signals for actuating devices of the internal combustion engine, which may be for example an injection valve, a throttle valve, an exhaust gas recirculation valve or the like.

The control apparatus 5 has a data and program memory, in which one or a plurality of programs for operating the internal combustion engine are stored, which programs can then be processed during the operation of the internal combustion engine. For this purpose, the control apparatus 5 also has a computing unit comprising, inter alia, a microprocessor and/or a controller. Furthermore, the control apparatus 5 also has one or a plurality of output stages.

Furthermore, lambda control is realized in the control apparatus 5, to be precise in interaction with corresponding actuating devices, such as, for example, the respective injection valves and the internal combustion engine and the linear lambda probe 3. In this connection, the measurement signal MS is fed to a block B1. The block B1 is designed to determine an actual value LAM_AV of the air/fuel ratio depending on the measurement signal MS. For this purpose, the block B1 preferably has a predefined characteristic curve and, if appropriate, a corresponding adaptation is also effected by means of a trimming value, which, if appropriate, is the output variable of a trimming controller and is determined depending on a measurement signal of a further lambda probe, in particular of a binary lambda probe, which is arranged downstream of an exhaust gas catalytic converter (not illustrated), which is in turn arranged downstream of the linear lambda probe 3.

This is used in particular for the compensation of the offset OFFS of the measurement signal MS. Such a procedure of compensation of the offset OFFS can also be designated as external offset compensation. A raw setpoint value LAM_SP_RAW of the air/fuel ratio is fed to a summing point SUM1, said value being determined in particular depending on one or more input variables of the control apparatus 5 and thus being determined for example depending on the operating state and/or depending on the operating point relative to the internal combustion engine.

In so-called lean operation of the internal combustion engine, the raw setpoint value LAM_SP_RAW has a super-stoichiometric value, while it has a substoichiometric value in so-called rich operation of the internal combustion engine. For operation with an air ratio of 1 or in particular approximately 1, the raw setpoint value LAM_SP_RAW has the stoichiometric value.

A setpoint value LAM_SP of the air/fuel ratio is formed at the first summing point SUM1 by a forced excitation signal ZWA being modulated on the raw setpoint value LAM_SP_RAW. The forced excitation signal ZWA preferably has a rectangular, periodically repeating profile. An amplitude of the forced excitation ZWA can be predefined differently, if appropriate, depending on the internal combustion engine or operating state. The same correspondingly also applies to the period duration of the forced excitation ZWA.

The forced excitation signal ZWA is designed such that, in the case of a stoichiometrically predefined raw setpoint value LAM_SP_RAW, the setpoint value LAM_SP deviates alternately from the stoichiometric value in each case by a few percent toward a lean mixture and, on the other hand, toward a rich mixture.

At a summing point SUM3, a control difference is formed depending on the difference between the actual value LAM_AV and the setpoint value LAM_SP. The control difference is fed to a block B3 comprising a lambda controller, which can be designed as a PID controller, for example. On the output side of the controller in the block B3, a lambda correction value is then provided as actuating signal of the lambda controller. At a multiplying point M1, said lambda correction value is combined multiplicatively with a fuel mass MFF_SP to be metered and a corrected fuel mass MFF_SP_KOR to be metered is thus determined. The latter is used for correspondingly driving the respective injection valve. The fuel mass MFF_SP to be metered is determined in a block B5, to be precise for example depending on a rotational speed and/or an air mass flow and/or an intake pipe pressure of the internal combustion engine.

For the operation of the linear lambda probe 3, various programs are preferably stored in the data and program memory of the control apparatus 5, which programs are explained in greater detail below with reference to FIGS. 2 to 5.

A first program is started in a step S1 (FIG. 2) in which case, if appropriate, variables can be initialized. The start preferably takes place in order to identify an error of the offset OFFS of the measurement signal MS of the linear exhaust gas probe 3, to be precise for example for the case of the external offset compensation and a short period duration of the forced excitation signal.

In a step S3, a check is made to ascertain whether the raw setpoint value LAM_SP_RAW of the air/fuel ratio is approximately, in particular exactly, stoichiometrically predefined. If the condition of step S3 is not met, then the program is ended in a step S5, since the offset OFFS cannot be checked in this case.

By contrast, if the condition of step S3 is met, then in a step S7 a fluctuation characteristic value SWKW is determined depending on a difference signal DS. The difference signal DS is formed depending on a difference between the pump voltage signal U_P and the Nernst voltage signal U_N. It represents this difference directly, for example.

In step S7, a check is then made to ascertain whether the fluctuation characteristic value SWKW is greater than a predefined first threshold value THD1. The latter is determined in particular by means of corresponding experiments on an engine test stand, for example or by means of simulations. If the fluctuation characteristic value SWKW is greater than the predefined first threshold value THD1 in step S7, then the absence of an offset error is identified in a step S9. By contrast, if the condition of step S7 is not met, then in a step S11 a check is made to ascertain whether the difference signal DS is representative of a purportedly lean operation of the internal combustion engine. If this is the case, then in a step S13 an offset error in the direction of a rich mixture is identified and the offset OFFS with regard to a rich shift is optionally determined.

By contrast, if the condition of step S11 is not met, then in a step S15 an offset error in the direction of a lean mixture is identified and the offset OFFS with regard to a rich shift is optionally determined.

A further program is started in a step S17 (FIG. 3), in which, if appropriate, variables can be initialized.

Figure 3:
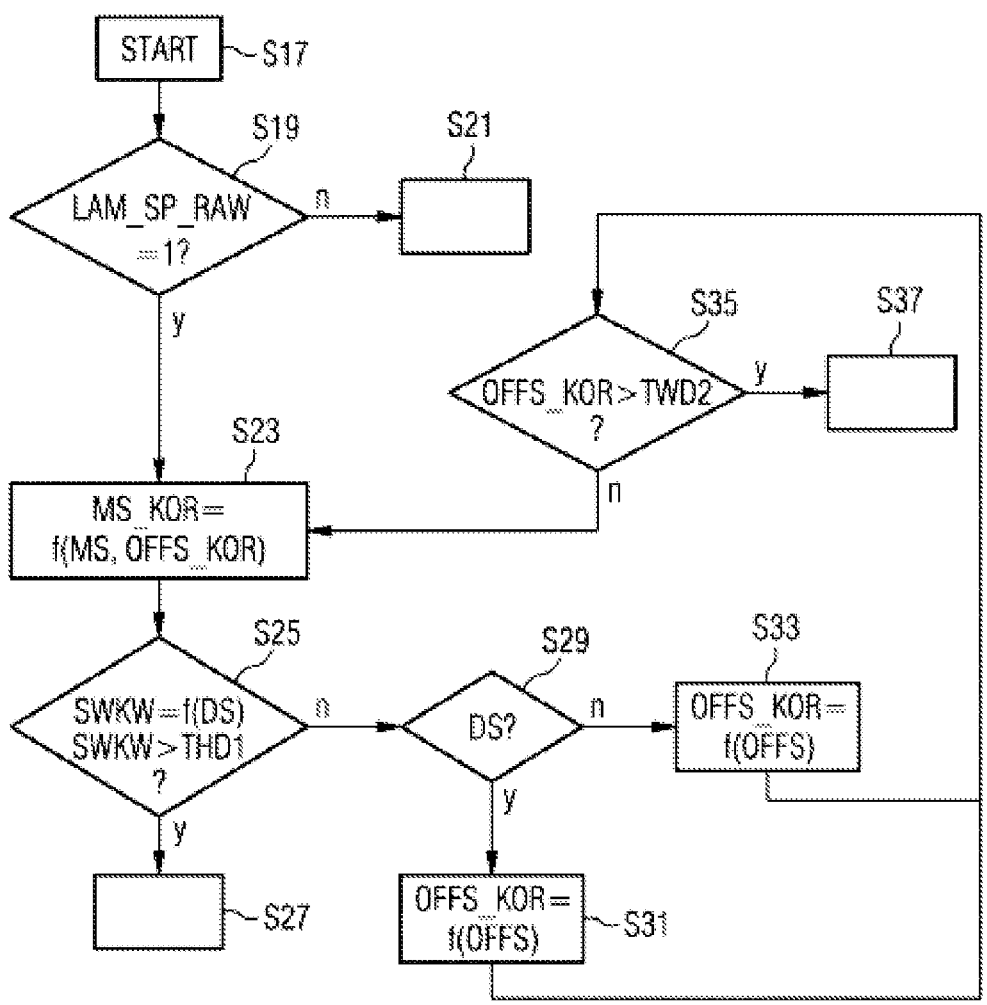
FIG. 3 shows a flow chart of a second program for operating the linear lambda probe.

The program in accordance with the flow chart in FIG. 3 is preferably started in step S17 with regard to an offset error identification for the case where no external offset compensation is carried out and the forced excitation signal ZWA has a short period duration.

Steps S19 and S21 correspond to steps S3 and S5, respectively. If the condition of step S19 is met, then the processing is continued in a step S23. In step S23, an internal offset compensation is initiated, to be precise by virtue of the fact that a corrected measurement signal MS_KOR is determined depending on the measurement signal MS and an offset correction value OFFS_KOR. In principle, the corrected measurement signal MS_KOR is determined in parallel also with the processing of other steps.

A step S25 corresponds to step S7. If the condition of step S25 is met, then the absence of the offset error is identified in a step S27 corresponding to step S9. If the condition of step S25 is not met, then a step S29 is carried out, corresponding to step S11. If the condition of step S29 is met, then a step S31 is processed, in which the offset correction value OFF_KOR is adapted. For this purpose, in step S31, the offset OFFS is determined as being in the direction of an excessively rich mixture and the offset correction value OFFS_KOR is correspondingly adapted depending on the offset OFFS.

By contrast, if the condition of step S29 is not met, then in step S33 the offset OFFS is determined as being in the direction of lean and is allocated a correspondingly suitable value and the offset correction value OFFS_KOR is adapted depending on the offset OFFS thus determined.

The processing is subsequently continued, to be precise after step S33 or respectively S31, in a step S35. In step S35, a check is made to ascertain whether the offset correction value OFFS_KOR is greater than a predefined second threshold value THD2. The second threshold value THD2 is determined beforehand in particular by means of corresponding experiments, thus for example on an engine test stand, or by means of simulation. If the condition of step S35 is met, then the presence of the offset error is identified in a step S37. By contrast, if the condition of step S35 is not met, then the offset correction value OFFS_KOR is subsequently used for the correction of the measurement signal MS.

A third program is started in a step S41 (FIG. 4), in which, if appropriate, variables are initialized. The third program is used for identifying an offset error in the case of an external offset compensation and a forced excitation signal having a long period duration.

A subsequent step S43 and a subsequent step S45 correspond to steps S3 and S5, respectively. If the condition of step S43 is met, then the processing is continued in a step S47. In step S47, a check is made to ascertain whether the difference signal DS has an expected profile. In this connection, a check is made to ascertain, for example, whether the difference signal DS correspondingly correlates with the setpoint value LAM_SP of the air/fuel ratio. If a corresponding correlation is identified in step S47, then the absence of the offset error is identified in a step S49.

Otherwise, the processing is continued in a step S51, corresponding to step S11. If the condition of step S51 is met, then the processing is continued in step S53, corresponding to step S13. By contrast, if the condition of step S51 is not met, then the processing is continued in a step S55, corresponding to step S15.

A fourth program is started in a step S59 (FIG. 5), in which, if appropriate, variables can be initialized. The fourth program is started in particular for identifying the offset error in the case of the absence of the external offset compensation and in the case of the forced excitation signal ZWA with a long period duration.

Steps S61, S63 and S65 correspond to steps S19, S21 and S23, respectively. After the processing of step S65, the processing is continued in a step S67, corresponding to step S47. If the condition of step S67 is met, then the processing is continued in a step S69, corresponding to step S49. If the condition of step S67 is not met, then the processing is continued in a step S71, corresponding to step S29. If the condition of step S71 is met, the processing is continued in a step S73, corresponding to step S31. If the condition of step S71 is not met, then the processing is continued in a step S75, corresponding to step S33. After the processing of step S73 or respectively step S75, the processing is continued in a step S77, corresponding to step S35. If the condition of step S77 is met, then the processing is continued in a step S49, corresponding to step S37.

FIG. 6 shows various signal profiles plotted against time t. Exemplary profiles of the difference signal DS, of the setpoint value LAM_SP and of the actual value LAM_AV are plotted in this case. A scaling of the respective values of the difference signal DS is relative to the second depicted ordinate as seen from the left and the corresponding values thereof, while the setpoint value LAM_SP and the actual value LAM_AV are relative to the first ordinate as seen from the left. The same correspondingly also applies to the signal profiles in accordance with FIGS. 7 and 8.

The signal profiles of the difference signal DS in FIGS. 6 to 8 are plotted by way of example in each case for an absence of the offset error and offset OFFS. They are illustrated within the individual diagrams, however, for different raw setpoint values LAM_SP_RAW which correspondingly deviate from the stoichiometric value. Accordingly, the profile of the difference signal DS is then correspondingly altered given the presence of the offset error or the offset OFFS.

FIG. 6 illustrates the profiles in the case of a forced excitation signal ZWA having a high amplitude and a short period duration. In FIG. 7, the period duration of the forced excitation signal ZWA is likewise short, but the amplitude is small. In the profile in accordance with FIG. 8, the period duration of the forced excitation signal ZWA is long and the amplitude of the forced excitation signal ZWA is also high.

In the case of a forced excitation signal ZWA in accordance with FIG. 7, the offset error can be identified with high selectivity, to be precise in a manner supported by the fluctuation characteristic value SWKW. In the case of the forced excitation signal ZWA having a high amplitude and long period duration, as in accordance with FIG. 8, for example, a correlation of the actual value LAM_AV with the temporal behavior and the amplitude of the difference signal DS is readily possible. However, exhaust gas propagation times between the metering of the fuel and the detection at the linear lambda probe result in a phase shift. In order to compensate for such influences, either they can be taken into account directly or an evaluation can also be carried out by means of the suitable fluctuation characteristic value SWKW, in which case here in particular an amplitude of the profile of the difference signal DS can be evaluated. In this case, for the case in which the fluctuation characteristic value SWKW falls below a suitable further threshold value, that is to say, in particular, the amplitude is smaller than the predefined further threshold value, a corresponding identification of an offset error in the direction of lean or rich can take place and, if appropriate, a corresponding adaptation of the offset correction value can take place.

In the case of a forced excitation signal having a small amplitude and a short period duration, in particular purely the statistics of the difference signal DS can be evaluated. In this regard, by way of example, the absence of the offset error can be identified in this case if a number of fluctuations of the difference signal with an amplitude greater than a predefined still further threshold value per time interval is greater than a number threshold value.

The procedure enables, in particular, a plausibilization of the offset OFFS of the measurement signal or corrected measurement signal MS_KOR of the linear lambda probe 3 from signals generated by the linear lambda probe 3 itself. In this way, an important diagnosis can be significantly simplified and it can be reduced in particular to the component to be diagnosed, in this case the linear lambda probe 3.

LIST OF REFERENCE SIGNS

1 Actuator can
1a Diaphragm
1b Restoring spring
1c Pressure chamber
2 Lever and rod system
3 Hose connection
4 Hose
5 Additional volume element
6 Hose connection
7 Hose connection
8 Control element
9 Waste gate flap
A Actuator

What is claimed is:

1. A method for operating a linear lambda probe arranged in an exhaust section of an internal combustion engine, the linear lambda probe comprising a first electrode exposed to an exhaust gas side, a second electrode and a third electrode arranged adjacent to a measurement chamber, and a fourth electrode arranged adjacent to a reference air volume, wherein solid electrolytes are respectively situated between the first and second electrodes and between the third and fourth electrodes and a diffusion barrier is formed between a free volume of the measurement chamber and the exhaust section, wherein a potential difference between the first and second electrodes forms a pump voltage signal and a potential difference between the fourth and third electrodes forms a Nernst voltage signal, the method comprising:
  determining a measurement signal of the linear lambda probe based on a pump current applied between the first and second electrodes, the measurement signal representing an air/fuel ratio of gas flowing in the exhaust section, prior to combustion of said gas,
  generating a difference signal based on a difference between the pump voltage signal and the Nernst voltage signal,
  determining a setpoint value of the air/fuel ratio based on a raw setpoint value of the air/fuel ratio and a forced excitation signal,
  determining whether the raw setpoint value of the air/fuel ratio is approximately stoichiometrically predefined, and
  in response to determining that the raw setpoint value of the air/fuel ratio is approximately stoichiometrically predefined, determining an offset error of the measurement signal based on the difference signal.

2. The method of claim 1, comprising determining an offset of the measurement signal based on a fluctuation characteristic value of the difference signal.

3. The method of claim 2, comprising:
performing a check to determine whether the fluctuation characteristic value exceeds a first threshold value, and
in response to determining that the fluctuation characteristic value does not exceed the first threshold value, determining the offset error or offset based on the difference signal.

4. The method of claim 1, comprising:
performing a check to determine whether the difference signal correlates with the setpoint value of the air/fuel ratio, and
in response to identifying no predefined correlation, determining the offset error or an offset of the measurement signal based on the difference signal.

5. A method for operating a linear lambda probe arranged in an exhaust section of an internal combustion engine, the linear lambda probe comprising a first electrode expose to an exhaust gas side, a second electrode and a third electrode arranged adjacent to a measurement chamber, and a fourth electrode arranged adjacent to a reference air volume, wherein solid electrolytes are respectively situated between the first and second electrodes and between the third and fourth electrodes and a diffusion barrier is formed between a free volume of the measurement chamber and the exhaust section, wherein a potential difference between the first and second electrodes forms a pump voltage signal and a potential difference between the fourth and third electrodes forms a Nernst voltage signal, the method comprising:
determining a measurement signal of the linear lambda probe based on a pump current applied between the first and second electrodes, the measurement signal representing an air/fuel ratio of gas flowing in the exhaust section, prior to combustion of said gas,
determining a corrected measurement signal based on the measurement signal and an offset correction value,
generating a difference signal based on a difference between the pump voltage signal and the Nernst voltage signal,
determining a setpoint value of the air/fuel ratio based on a raw setpoint value of the air/fuel ratio and a forced excitation signal,
determining whether the raw setpoint value of the air/fuel ratio is stoichiometrically predefined,
in response to determining that the raw setpoint value of the air/fuel ratio is approximately stoichiometrically predefined, determining an offset of the corrected measurement signal based on the difference signal, and
adjusting the offset correction value based on the determined offset.

6. The method of claim 5, comprising determining the offset of the measurement signal based on a fluctuation characteristic value of the difference signal.

7. The method of claim 6, comprising:
performing a check to determine whether the fluctuation characteristic value exceeds a first threshold value, and
in response to determining that the fluctuation characteristic value does not exceed the first threshold value, determining the offset based on the difference signal.

8. The method of claim 5, comprising:
performing a check to determine whether the difference signal correlates with the setpoint value of the air/fuel ratio, and
in response to identifying no predefined correlation, determining an offset of the measurement signal based on the difference signal.

9. An apparatus for operating a linear lambda probe arranged in an exhaust section of an internal combustion engine, the linear lambda probe comprising a first electrode expose to an exhaust gas side, a second electrode and a third electrode arranged adjacent to a measurement chamber, and a fourth electrode arranged adjacent to a reference air volume, wherein solid electrolytes are respectively situated between the first and second electrodes and between the third and fourth electrodes and a diffusion barrier is formed between a free volume of the measurement chamber and the exhaust section, wherein a potential difference between the first and second electrodes forms a pump voltage signal and a potential difference between the fourth and third electrodes forms a Nernst voltage signal, the apparatus comprising:
a processor, and
computer instructions stored in non-transitory computer-readable media and executable by the processor to:
determine a measurement signal of the linear lambda probe based on a pump current applied between the first and second electrodes, the measurement signal representing an air/fuel ratio of gas flowing in the exhaust section, prior to combustion of said gas,
generate a difference signal based on a difference between the pump voltage signal and the Nernst voltage signal,
determine a setpoint value of the air/fuel ratio based on a raw setpoint value of the air/fuel ratio and a forced excitation signal,
determine whether the raw setpoint value of the air/fuel ratio is approximately stoichiometrically predefined, and
in response to determining that the raw setpoint value of the air/fuel ratio is approximately stoichiometrically predefined, determine an offset error of the measurement signal based on the difference signal.

10. The apparatus of claim 9, wherein the computer instructions are configured to determine an offset of the measurement signal based on a fluctuation characteristic value of the difference signal.

11. The apparatus of claim 10, wherein the computer instructions are configured to:
perform a check to determine whether the fluctuation characteristic value exceeds a first threshold value, and
in response to determining that the fluctuation characteristic value does not exceed the first threshold value, determine the offset error or offset based on the difference signal.

12. The apparatus of claim 9, wherein the computer instructions are configured to:
perform a check to determine whether the difference signal correlates with the setpoint value of the air/fuel ratio, and
in response to identifying no predefined correlation, determine an offset of the measurement signal error or the offset based on the difference signal.

* * * * *